(12) United States Patent
La Clair (10) Patent No.: US 7,706,984 B2
(45) Date of Patent: Apr. 27, 2010

(54) METHOD AND DEVICE FOR IDENTIFYING MOLECULAR SPECIES

(75) Inventor: James J. La Clair, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 463 days.

(21) Appl. No.: 10/797,900

(22) Filed: Mar. 10, 2004

(65) Prior Publication Data

US 2004/0229254 A1 Nov. 18, 2004

(51) Int. Cl.
*G06F 19/00* (2006.01)

(52) U.S. Cl. ........................................ 702/27
(58) Field of Classification Search ................ 702/22, 702/27
See application file for complete search history.

(56) References Cited

U.S. PATENT DOCUMENTS

| | | | | |
|---|---|---|---|---|
| 5,122,284 | A | 6/1992 | Braynin et al. | 219/782 |
| 5,850,195 | A * | 12/1998 | Berlien et al. | 341/137 |
| 5,968,728 | A | 10/1999 | Perttunen et al. | 435/4 |
| 6,030,581 | A | 2/2000 | Virtanen | 422/68.1 |
| 6,048,692 | A | 4/2000 | Maracas et al. | 435/6 |
| 6,099,803 | A | 8/2000 | Ackley et al. | 422/68.1 |
| 2002/0004204 | A1* | 1/2002 | O'Keefe | 435/6 |
| 2006/0228708 | A1* | 10/2006 | Smilansky | 435/6 |

FOREIGN PATENT DOCUMENTS

EP 1189062 A1 11/2005

OTHER PUBLICATIONS

Merriam-Webster Online Dictionary "digital" http://mw1.merriam-webster.com/dictionary/digital (site last visited May 14, 2007).*
Elkins, R. , et al., "Multianalyte Microspot Immunoassay, the Microanalytical 'Compact Disk' of the Future", *Annales de Biologie Clinique*, 50(5), (1992),337-353.
Kapur, Ravi , "Streamlining the Drug Discovery Process by Integrating Miniaturization, High Throughput Screening, High Content Screening, and Automation on the CellChipTM System", *Biomedical Microdevices*, 2(2), (1999),99-109.
La Clair, J. J., et al., "Geometry in digital molecular arrays.", *Org Biomol Chem*. 4(16), (2006),3052-5.
La Clair, J. J., et al., "Molecular screening on a compact disc", *Org Biomol Chem.*, 1(18), (2003),3244-9.
Najmabadi, P. , et al., "A systems perspective to digital structures in molecular analysis", *Org Biomol Chem.*, 5(2), (2007),214-22.

* cited by examiner

*Primary Examiner*—Jerry Lin
(74) *Attorney, Agent, or Firm*—Schwegman, Lundberg & Woessner, P.A.

(57) ABSTRACT

The invention relates to a device and a method for analyzing the interaction between one or more molecular species the method comprising the steps of creating streams of digital data, transferring the stream of digital data through a substrate, manipulating the molecular structure of the substrate by adding or subtracting molecules or groups of molecules to be examined to or from the substrate, receiving the streams of digital data transferred through the substrate, decoding the identity of an examined molecule or group of molecules interacting with the substrate by deciphering how the molecules affinity to another molecule or group of molecules or molecular sensor or group of molecular sensors alters the stream of digital data. The invention relates further to a method for identifying molecular species, and to a device for identifying molecular species and to a substrate for analyzing the interaction and for identifying molecular species.

20 Claims, 10 Drawing Sheets structural characterization diagnostic analysis

Recognition

Aggregation

Reactivity

METHOD AND DEVICE FOR IDENTIFYING MOLECULAR SPECIES

The invention relates to a method for analyzing the interaction between one or more molecular species, to a method for identifying molecular species, to a device for analyzing the interaction between one or more molecular species and to a device for identifying molecular species, and to a substrate for analyzing the interaction and for identifying molecular species.

The physical health and identity of an organism can be characterized by the expression of a marked group of molecular species. Information given by these molecules, while used concertedly by the organism, can currently divided into groups of molecular classes or groups (e.g., fats, nutrients, vitamins, proteins and genes). For each of these groups, a series of analytical techniques have been developed to address the identity, expression and reactivity of a given molecule or class of molecules.

Currently, these techniques distinguish a molecule either by characterizing the molecule s three-dimensional atomic structure or gathering information based on how the molecule interacts with other molecules. This differentiation is demonstrated using 4-nitrophenol (1). Structurally, one can identify an unknown molecule as 4-nitrophenol when its atomic architecture matches that illustrated in upper portion of FIG. 1. The structural features of a molecule (3) are currently determined using a combination of x-ray crystallography, mass spectroscopy, nuclear magnetic resonance spectroscopy, and elemental analysis. These tools provide a means to characterize. Application of these or related methods is herein referred to as structural characterization (3).

Figure 1:
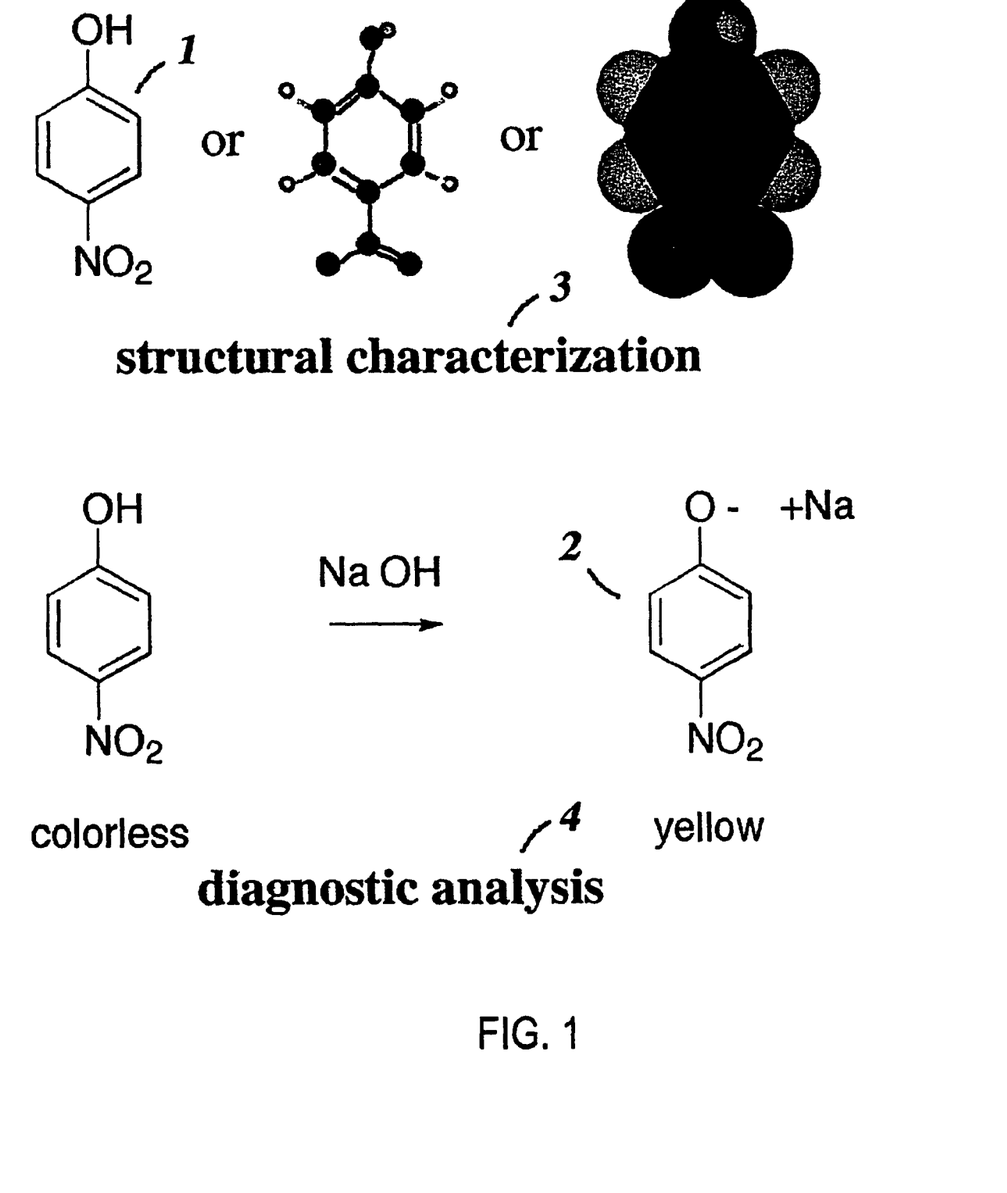
In FIG. 1, technologies used are described to distinguish a molecule (1-2) relying on methods that identify a molecular species either by characterizing its structure (3) or monitoring how this species interacts with other molecules in its environment(4). The first approach (3) is entitled structural characterization, and the latter (4) are diagnostic analysis.

The second class or diagnostic techniques (4) classify a molecule by examining how application of an entity alters the way in which a given molecule interacts with a group of other molecules, termed a sensing element. As illustrated in the bottom of FIG. 1, 4-nitrophenol can be identified by the appearance of a bright yellow color (2) upon adding an aqueous solution of sodium hydroxide. Here, the user's eye acts as the sensor and the addition of sodium hydroxide functions as what is defined as a manipulator. The study of the photophysical, kinetic and thermodynamic properties of this response also serves to further detail the identification of 4-nitrophenol (1). Modern molecular diagnostics employ a variety manipulators and sensors, based highly refined magnetic, electrical, optical, thermal and physiochemical fields. The molecular specificity of each diagnostic tool is therein defined in terms as a function of its manipulator and the selectivity of its sensor.

Recent advances in molecular diagnostics have arisen from learning how to correlate a photophysical, electrochemical or spectroscopic events with a stationary two-dimensional space as used in fluorescent or electronic micro-arraying, a floating three-dimensional object, as seen in bead screening technologies, a miniscule volume element as seen in single molecule spectroscopies, or digital optics. Each of these approaches is based on a prescribed information flow. This flow is not a real entity, but rather outlines a transfer of information. The organization of this flow can dramatically expedite and enhance the resolution of molecular analyses as it has been described in U.S. Pat. Nos. 6,060,023, 6,048,692, 5,968,728.

Figure 2:
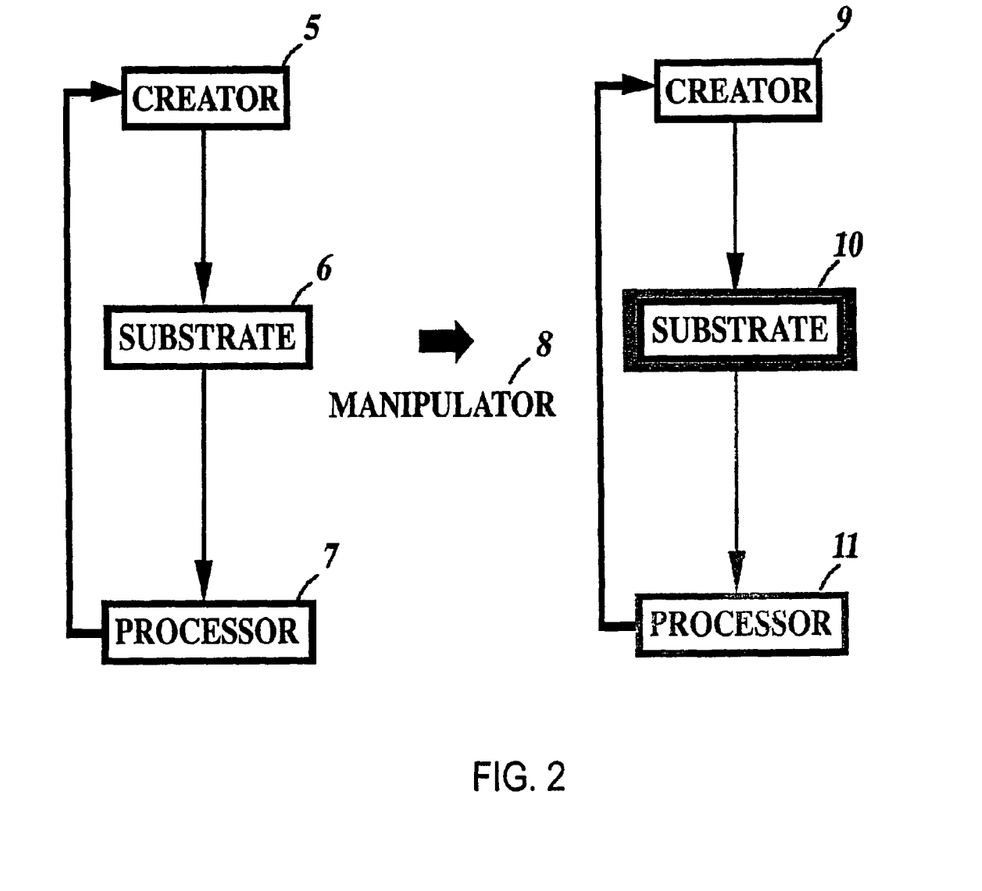

Partly, a new operating system is revealed to outline the information flow for molecular diagnostics. As it is further outlined in FIG. 2, this system exists within three functional units, namely, a creator (5 or 9), a substrate (6 or 10) and a processor (7 or 11). Information begins at the creator (5 or 9). Usually, the creator (5 or 9) is either a person or software system or computer or robot that organizes or maps a list of molecular queries. The creator (5 or 9) purpose is to encode each sensor or sensing element so that it recognizes a given molecule or class of molecules (i.e., sensor A1 to molecule 1, sensor A2 to molecule 2, etc.). This information is then incorporated into a native substrate (6). The native substrate (6) transmits the creator's information at a given molecular state. The native substrate is, in turn, exposed by application of a manipulator (8). The manipulator (8) is an entity or group of entities that alters the molecular composition of the substrate. These entities can either be a physical force, a geometric dimension, time, or a collection of molecular species. In this operating system, information sent from the creator passes through native and exposed substrates (6 and 10) to the corresponding processor (7 and 11). As illustrated in FIG. 2, molecular information is diagnosed by comparing the structure of the digital data set received at the native and exposed states (7 and 11 respectively). The operation of a series of the state of the art molecular diagnostics is outlined using this processes in the following paragraphs.

Microarray Technologies

Affinity microarraying has become an integral element for genetic resequencing, arising in part from the tremendous information density stored within these methods. While not limited to genetic screening, the designs of these methods demonstrate by the method of microarraying. Affymatrix' GeneChips™ (U.S. Pat. No. 6,040,138) and Incyte's GEM™ Microarrays (U.S. Pat. No. 6,004,755) decode gene expression based on the association of fluorescently tagged strands of c-DNA or m-RNA. These techniques select specific genes by monitoring complementation of targeted genes with matrixes thousands of oligonucleotides. Other methods such as Sequenom's MassARRAY™ (U.S. Pat. Nos. 6,074,823, 6,043,031) combine mass spectroscopy with comparable affinity matrixes.

Figure 3:
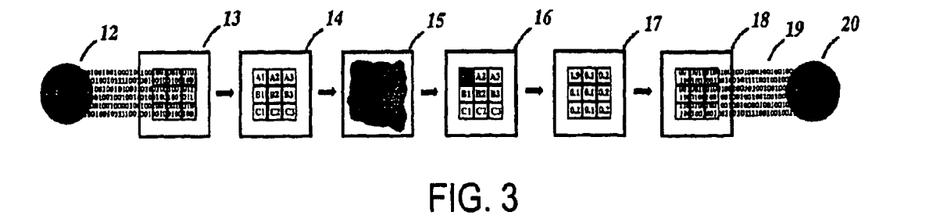

For these known technologies, the creator (12) is a computerized-robotic system that translates binary code to a positional-array of oligonucleotides. Here, creator (12) not only initiates data flow but also maps a series of substrates or reagents on chip (13). As illustrated in FIG. 3, the creator converts a digital code into spatially-addressed array of gene sensors by arranging, printing or synthesizing a series of oligonucleotides in specific quadrants on a glass or silicon surface, as shown by progression from 12 to 14. In (13), each examined gene or group of genes is identified by its localization within a given region of the two-dimensional surface or chip, based on its affinity to the array of oligonucleotides. This chip then becomes the substrate (14). The manipulator exposes substrate (14) with sample of genetic material (15) and follows this operation by inducing it either with an appropriately tuned laser beam or an electrical flow (16). The intensity of this alteration (17) is via (18) converted back to a digital code (19) and sent to a personal computer processor (20). Note that while several steps were required, the net input and output of this system is digital binary code. For all of these systems, the code used by creator (12) differs from than that used by processor (20).

Recently, these techniques have been expanded to microelectronic systems (U.S. Pat. No. 6,099,803) that can map and read both genetic and protomic information. These systems again employ a different coding for both creator (12) and processor (20). As indicated, creator (12) generates an array of sensor molecules (14) using a microelectronic system that organizes the molecule sensors in a given two dimensional array. After exposure to a given manipulator (15), reacted or positive sensing are then concentrated to a smaller volume elements using a second set of microelectronic commands and detected optically (16-17). While this development, expedites the digital encoding (18) and transmission to the processor (20), the codes used by the creator (12) and processor (20) as defined in within U.S. Pat. No. 6,099,803 remain unrelated.

Combinatorial Bead Screening Technologies

Figure 4:
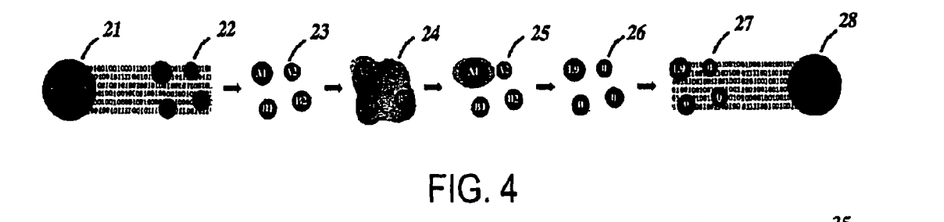
In FIG. 4, combinatorial bead screening technologies is described encoding the identity of a molecular species not by tagging the molecular species, rather by encoding the molecules with a tagged bead. Bead methods advantageously allow rapid selection without altering the structure of the examined molecule. Here, the creator (21), usually computer-operated synthetic robot, maps the array of diagnosed molecules in terms of each bead (22). The beads are then pooled, manipulated (24-25) and then examined using fluorescence or other spectrochemical methods (26). Again, the creator (21) and processor (28) operate in terms of two different digital codes.

Bead-screening technologies have gained utility for both genetic, pharmaceutical and materials screening. For example, bead systems developed by Pharmacopoeia (U.S. Pat. Nos. 6,001,579, 5,721,099, 5,565,324) have demonstrated means to expedite materials and drug screening. These techniques have also gained utility to screen gene and protein pools (Walt, 1999). As illustrated in FIG. 4, these methods encode molecular information over three-dimensional space. Here, creator (21) attaches each molecular query to a uniquely "tagged" bead (22). Each unique tag identifies a specific a molecular feature or property and correlates it with a bead. These beads (23) then serve as the substrate, wherein they are pooled, exposed to sample (24) and then decoded using combinations of a variety of spectroscopic methods (25). The resulting data (26) is then transferred to a digital code (27) then sent to the processor (28). Again, the digital codes used by the processor (28) and creator (21) differ.

Single Molecule Spectroscopy

Figure 5:
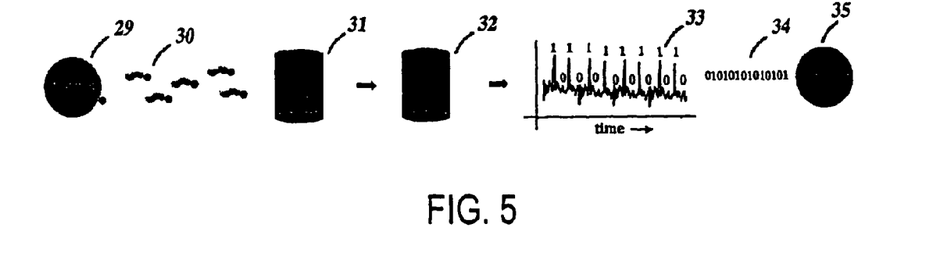
In FIG. 5, the solution-based single molecule fluorescence spectroscopy is described correlating molecular information with time by examining the diffusion of a molecule or cluster of molecules over a small volume element. As illustrated here, the identity of a fluorescent or fluorescently tagged molecule is given by bursts of fluorescent photons as the molecule diffuses through a conical optical cavity (32). Each molecule or molecular query (30) can be presented to the optical cavity (31) either by computer-operated robotics or flow. This function is the creator (29). These bursts are then converted (33) into a second digital code (34) and transmitted to a processor (35). Again, the creators (21) and processor's (35) coding systems differ.

Within the last decade, fluorescence spectroscopy and electrochemistry have been refined to the single molecule level through the device of sub-picoliter volume element (31). A series of techniques (U.S. Pat. Nos. 6,049,320, 5,933,233, 5,807,673) have been developed to define molecular identity on an individual basis by con-elation through time and space. As illustrated in FIG. 5, the single molecule creator either a person or computer driven robot (29) releases molecules (30) into a given space where within time (29) can diffuse through a miniscule cavity (31). This releasing can be organized in terms of a digital code. For these methods, the cavity serves as the substrate. When the molecule passes through the cavity (32) an electron or photon field is altered. Signals from this alteration (33) are digitally transformed (34) and sent to processor (35). Again, the digital codes used by both creator and processor differ.

Biocompact Discs

Figure 6:
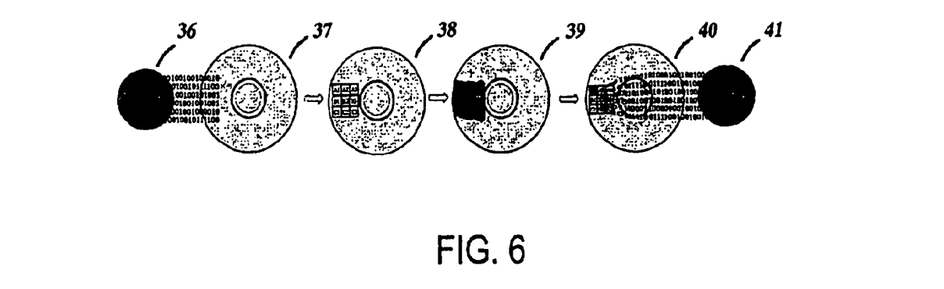
In FIG. 6, biologically addressed compact disc systems advantageously are described, providing an output that is readily communicated with conventional computer. As indicated, molecular information is mapped on a disc through a series of production stages. The creator (36) prepares each disc (37) with a given set of molecular queries. The loaded disc (38) is then exposed to sample-manipulator (39), and the outcome (40) of this function is transmitted to the processor (41) by digitally-scanning the disc in a compact disc player. As indicated in U.S. Pat. No. 6,030,581, this method requires generation of a digitally-encoded surface by either adhering gold or opaque spheres to a surface or blocking the reading of pre-encoded surface either opaque or fluorescently-labeled spheres.

Another class of modern analytical tools has arisen by attempting to devise systems that mimic the digital storage and transmission systems used in modem microelectronic devices. One venue has focused on developing disc-shaped cassettes for molecular assays based on screening with UV-visible spectroscopy or centripetal analyses (U.S. Pat. Nos. 5,122,284, 5,472,603, 5,173,193, 5,061,381, 5,304,348, 5,518,930, 5,457,053, 5,409,665, 5,160,702, 5,173,262, 5,409,665, 5,591,643, 5,183,844, 5,122,284, and 5,242,606). These systems have been extended to a biological compact disc system (U.S. Pat. No. 6,030,581). This system, composed of capillary ducts, valves, batteries, dialyzers, columns, filters, sources of electric fields, wires or other electroconductive materials, is devised to decode molecular information based on using the conventional optical system of a CD or DVD player to monitor localizing reflective particles onto a transparent surface or opaque particles onto a reflective surface. The identity of a molecule is encoded by monitoring how molecular association can alter the diffusion reflective elements. As illustrated in FIG. 6, the creator either a person or a computer or a robot defines series of elements within the disc (36). Each element is defined such that it recognizes and binds a given molecule or series of molecules (37). These elements may include using information deposited into directly into the reflective surface (38). The creator (36) also can coats micrometer-sized gold or opaque spheres with a series of molecule that will recognize and bind the element. These disc and their associated spheres (38) serve as the substrate. Upon mixing with biological probes tagged spheres adhere to the surface in a means that directly correlates with the identity of a each molecular species (39). The adhesion between the sphere and element creates either an opaque or reflective surface. As described in U.S. Pat. No. 6,030,581, these surfaces can then be read directly in a compact disc player by the observation of again a loss or gain in reflectivity. The observed signal (40) is then efficiently translated by a using the CD or DVD player into a digital code that is directly passed to personal computer (41). The use of a compact disc reader efficiently expedites conversion of the processed code. However, the code given by the creator (36) and processor (41) remain unrelated.

It is therefore an object of the present invention to provide a method or device for analyzing the interaction between one or more molecular species or a method or a device for identifying molecular species or a substrate in order to facilitate the diagnostic methods, for example, known in the prior art.

This object is solved by the features of independent claim 1, 2, 11, 12 and 21.

According to the invention, the method for analyzing the interaction between one and more molecular species and the method for identifying molecular species comprises the steps of creating streams of digital data, by which it is detectable if a molecular species is present. Moreover, the invention extends technology in field of bioelectronics and describes a cybernetic approach to collect and interpret molecular information. In particular, this disclosure extends an operating system, entitled ditom, to digitally code the identity, reactivity and/or expression of a given molecular species. This operating system can be applied to enhance the operation of wide range molecular screening technologies, wherein the dimensions of time, space and matter are integrated over a fourth or cybernetic dimension.

SUMMARY OF INVENTION

As defined by Einstein s theory of relativity, information is defined into packets of energy is in turn divided among dimensions of time, space and matter. Of which the latter dimension can also be defined in terms of molecular space or molecules. In 1947, Wiener introduced the concept of a fourth dimension called cybernetics, wherein information or intelligence is encoded by an attribute of an interaction (Wiener, N. 1948). In the early 1950's Turing systems are one of the most appropriate means to describe the information dimension and became the norm for cybernetic systems upon the discovery of the transistor. Within the last decade, digital electronics has tremendously expanded the boundaries of information transfer, wherein the dimensions of time and space are currently identified cybernetically on a global basis. However at the current state of the art, matter can not be directly transformed to this dimension. The subject matter of the present invention describes an operating system, called ditom., to introduce molecules to the dimensions of cybernetic information.

The operating system of ditom is defined as any physical or mathematical element that gathers information about molecules or molecular species by examining how a molecule or group of molecules directly alters the flow of a digital stream. The operating system inputs molecules and outputs their identity, reactivity and/or expression directly in the form of strings of digital code. The principles of this method and applications extend a direct conduit between molecular and digital information, and generate a primary system to communicate and network molecular intelligence. This operating system can be applied to assemblies that have ready contact with current cybernetic instruments, such as microprocessors, microelectronic boards, or optical or magnetic storage systems, and can subsequently be extended to systems that are tailored to optimize molecular resolution.

All information expressed cybernetically is created and translated in terms of physical entity. Whether, a cable, electronic component, air or fluid, these physical entities serve as a means to conduct as well as host a digital signal. The operating system of ditom provides a method to understand the union between molecules, hence matter, and cybernetics. The simplicity of the physical structures employing these systems and those defined therein extend tools that will allow rapidly contact and communicate the information stored within a molecule.

Further advantageous designs and embodiments are subject of the remaining dependent claims.

BRIEF DESCRIPTION OF THE DRAWINGS

In FIG. 2, an outline of the methodology used for molecular diagnostics is described. In a native state creator (5) creates information and passes it to a processor (7) through a given substrate (6). The processor (7) can use this information to drive the creator (5). When an unidentified molecule is added by the manipulator (8), the system becomes exposed. In the exposed state, the creator (9) now passes information to processor (11) however though an altered substrate (10). This alteration changes the response or message received at (11). Again, the processor can again use its information to guide its creator (9).

In FIG. 3, the method of surface microarraying is described, which begins with a computer, or creator (12), that digitally maps affinity labels on a prescribed surface (13). After generation, these affinity matrixes (14) are exposed to a biological sample (15). The term biological sample is defined as any collection of molecular matter obtained from a living organism. After the appropriate incubation and processing (16), the surface of chip screened. This screening process can be preformed using range of spectroscopic tools (17). Currently, fluorescence spectroscopy is the most common tool used for microarrayed genetic resequencing. These methods require that the analyzed genetic material expressed within the biological sample undergo prior tagging with a fluorescent probe. Adhesion of the analyte is then monitored in two-dimensional space using confocal microscopy or flying wheel laser-induced fluorescence (16-17). The observed fluorescence photons are then counted (17) and then transcribed (18) to a second digital code (19) and sent to a processor (20).

In comparison to FIGS. 3-6, in FIG. 7 ditom defines molecular information by directly correlating an identifiable molecular transition with the transmission of a digital stream.

An operative structure for ditom according to FIG. 10 arises by correlating a biotic with diotic layers. A distinct set of biotic and diotic units are given for each individual piece of molecular information. The biotic layer serves to support the biological information and contains receptors or assemblies of the like that attracts and attaches to a specific molecular entity (M). Each receptor or assembly is packed in to a unit called a mobit (87). These mobits are then geometrically assembled into a mobyte (86). The biote is the comprised of series or arrays of mobits. A diote is the cybernetic equivalent of the biote. It expresses a digital or mathematic code within time or space in a sequence wherein each molecule (M) is encoded by a given sequence or molecular tag or mol tag (93). These mol tags (93) are then combined with a positional or temporal guide called a header (90) and packed into a unit called a MOL (92). Header (90) can come either before, during or after (93). MOLs (92) are then packed into a second unit called aXEL, which are then packaged again with (90), and a 12 bit sync (89) into a ORG. The sync (89) serves tracking of a given or with relation to other ORGS. These ORGs are then packaged into an SPX. Each SPX consists of a 16-bit identifier (88) that is used to indicate the method used and a series of ORGs organized either in series, arrays or mosaics.

Molecular processes that can be screened using a ditomic operator is shown in FIG. 11.

DETAILED DESCRIPTION OF THE INVENTION

I. Definitions

Biote is defined as a principle unit of biological information used by the ditom. The Biote is broken down into units of mobytes, which are in turn broken into units of mobits.

Digital flux refers the alteration of a constant or programmed digital string, stream or field.

Ditom refers to an operating system that gathers molecular information by selectively classifying and/or diversifying molecules based on the ability to disrupt the flow of a stream of digital data. Information gained from the collection and subsequent processing of the disrupted digital signal provides a tool to determine the identity, concentration and/or reactivity of a select molecule or groups of molecules. This operating system is applied to any system that obtains molecular information by monitoring an alteration in the transmission of a digital code. Diote is the digital complement to the biote. This component is broken down in units of SPXs, which is in turn broken down into units of ORGs, which is in turn broken down into units of XELs, which is in turn broken down into units of MOLs. Manipulator is defined as physical processes, force or entity that can alter the molecular structure of a given substrate. Mobyte is a single unit of molecular information or so called molecular byte. The mobit is comprised of mobits Sensor is defined a unit that can translate molecular information into a electrical, chemical or physical force. Substrate is defined as a unit that can conduct digital string, stream or field. Molecular Space is defined as the compilation of structural, chemical and physical properties of the molecular components of a given system. Namely, the molecular space for a crystal of salt is namely sodium chloride and water.

II. General a. Introduction

As it has been shown, diagnostic systems currently are composed of a creator that digitally encode a single or group of molecular queries. This code is not a physical entity, rather it represents a function defined by either an optical or magnetic or electronic phenomenon. This code is then conducted through a substrate in terms of thermal photonic or electronic gradient to a processor. The components of all substrates whether a channel, field, nanostructure, track, or wire can be altered by the addition of a given molecular species. This modulation serves to identify the aforementioned species. While often an integral part of molecular diagnostics, the current methodology used to diagnose molecular information is defined only in terms of a physical or chemical event.

For instance, one can identify a molecule by presence of a ketonic carbonyl group through examining its absorption of infrared light at 1810 nm. Looking at guidelines given by current scientific publications, this band would be recorded in terms of intensity and wavelength, units defined within dimensions of time and space. However, this response can also be viewed in cybernetically by identification with a given code. Such systems underlie the creation of genetic, proteomic and small molecule databank. For illustration purposes, one could devise a four byte code stating that a molecule with an absorption at 1810 nm comparable to that of a molecule of acetone would have a byte of 1111, =500% of that 1110, 400-500% of that 1101, 300-400% of that 1011, 200-300% of that 0111, 100-200% of that 1100, 75-100% of that 1001, 50-75% of that 0011, 25-50% 1000, 0-25% 0001 and 0% at 0000.

Ever molecule could then be defined in terms of these bytes. However, development of such systems require infinite analyses associated with the continuously adapting molecular structure, not to mention the complexities associated with determining the infrared spectra of single molecules. While these complexities are remedied by structural analyses, detailed identification of the structure of every molecule also remains impossible. Another way to approach such processing arises through giving each possible molecular structure a unique code. The physical meaning this code is irrelevant, rather it serves only as a descriptive element that can be theoretically expanded to cover all possible molecular mutations. This code can then be used as a tag or identity belt for molecular communications and serves as the cornerstone for the operating system of ditom.

Figure 7:
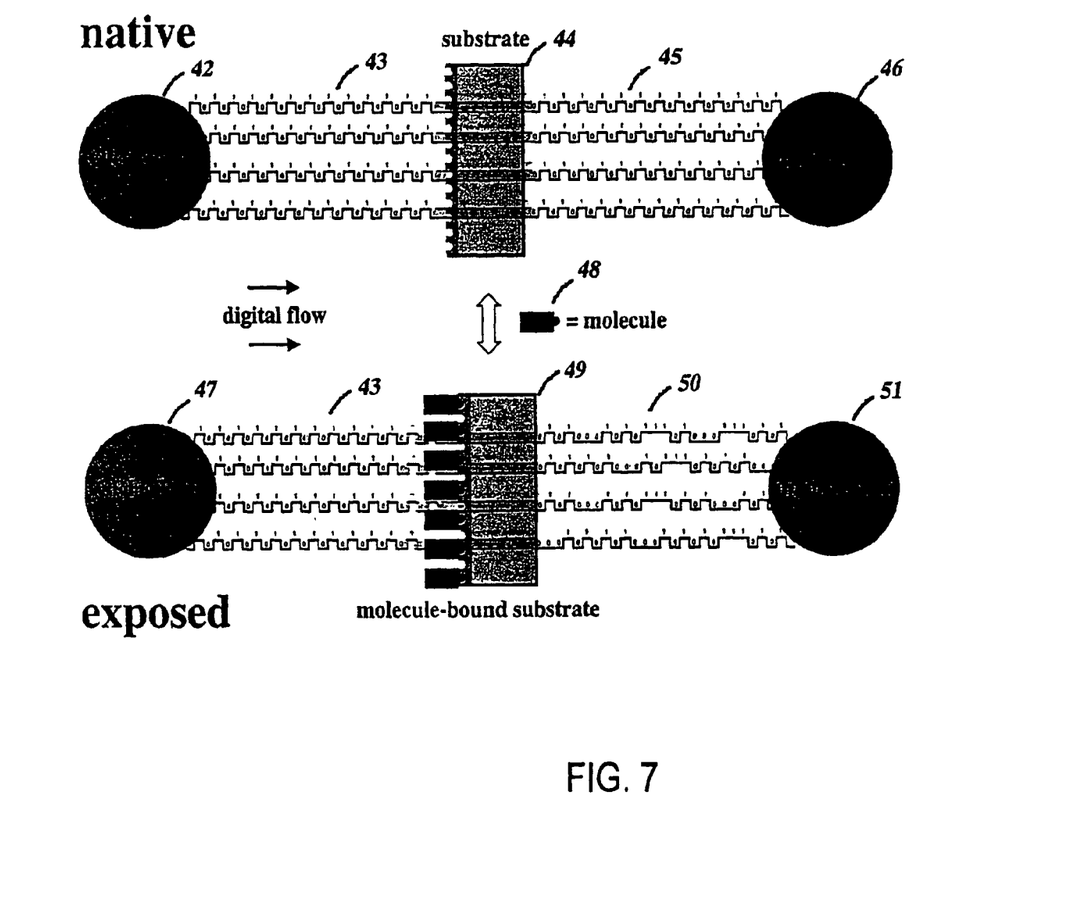

An overview of the ditomic operator is provided in FIG. 7. A defined digital code (43) generated by a creator (42) is transferred through substrate (44) to a processor (46). In the native state, the code (45) received by the processor (46) is either identical or a function of that generated by the creator (43). The manipulator (47) can alter a specific molecular even on substrate (44). This event converts (44) to (49) and scrambles the digital code. As illustrated the exposed creator (47) again generates (43). These digital streams are scrambled as they passes through (49) generating a new set of data (50). The structure of (50) then represents a function containing terms that describe the identity of molecular event that was altered. Here, both the creator and processor use a single code. For optimal performance, the processor (46 or 51) can either be in contact with or be the same unit as creator (42 or 46).

In this embodiment, the identity of this digital stream is given by the organization of each bit as it leaves at the creator (42 or 47), defined as the data set [M] (43) which serves to specifically identify a given molecule M. Under the native state, the substrate remains cybernetically transparent and the data generated by creator (42) reaches the processor (46) with minimal or constant or programmable alteration. Hence, the processor obtains a data set equivalent to [M]+[A] (45), were [A] represents a constant or algorithmic function. Native substrate (44) can be switched to an exposed state (49) upon addition of a given molecular species by manipulator (48). When exposed, molecules are either applied to or removed from the substrate. This application alters the ability of the creator to properly transmit native data set [M] (43). In the exposed state, the data (43) sent from creator (42) and received (50) at the processor (51) differ. This difference is referred to herein as digital flux, symbolized by $\zeta$ and is equal to [M]exposed−[M]native or [M]exposed−([M]+[AJ]. This flux can be used to qualify and/or quantify molecular species by integration over geometric temporal and molecular space, as defined as dz by:

$$d\zeta = {}^a\!\!\int \zeta(x)dx \qquad \text{Eq. 1}$$

wherein, x is defined as a variable defined in either position, time or molecular feature.

In one embodiment, the operating system of ditom can be employed to integrate molecular information over a two-dimensional space. Namely, x in Eq. 1 is given in dimensions of space. One structure of this operation is provided in FIG. 7.

As illustrated, the x- and y-axes are given in units of geometric surface, and serve to identify matter in terms of a distance. The z-axis represents information transport conducted either by a flow of atoms, electrons, photons, or molecules. This operating system is illustrated by defining a means to specifically-identify any given molecule α. One surface of a substrate is coated with matrix of three molecular receptors, depicted by letters A, B and C. Only receptor A recognizes and binds to the free-floating molecule α. B and C do not bind α. Arrays of each receptor are placed within mosaics of biotes, and are loaded within a biotic layer (58). A second or diotic layer (59), containing a physical system that presents a binary code, is placed upstream of each biote. The layering is designed such that the digital code must pass through the biotic layer. The structure of this diotic code defined such that each set of bits, or byte correlates with the identity of surface-bound receptor.

In this embodiment, a two-dimensional surface is defined with an upper surface (58 or 60) containing a series of repetitive biochemical sensors (A, B, C). A second or diotic layer (59 or 61), containing a physically encoded digital system, imbedded in a manner that correlates with the structure of the biological or biotic surface (58 or 60). The construct is defined such that the digital data must be read (52-57) through the biotic surfaces. For purposes of demonstration, this data (58-59) is assigned in a native state such that a byte of 00 lies under A (62), 01 under B (62), and 11 under C (64). After exposure to a biological sample containing a database of molecular species, molecules of a adhere to the surface of the chip (60) at positions where receptor A is expressed. The binding of α to A alters of the surface of the chip and distorts transmission of the underling digital code [M], depicted here by blurred arrow (55) or the outputs of reading this disc (65). This disruption creates a flux ζ. This flux refers to a predefined as geographical position, and serves to identify molecule α by its binding to receptor A. Given that surface modification occurs only at positions where A and α meet, the flux α would theoretically appear in bytes of 00. The data sets (62-67) depict the theoretical outcome of this experiment. In the native state, [M] reaches the detector unaltered by the nature of biotic surface. After exposure to molecule α, ζ appears in the code stored under receptor A (68). Note: that (65) differs from (62) while both (63) and (66) and (64) and (67) remain the same. The difference between the native and exposed sets called flux (68-69). This flux provides a handy tool to identify a molecular species by integration over a geometrical space.

In another embodiment, the operating system of ditom can be employed to integrate molecular information over time, as indicated by defining x in Eq. 1 in units of time. The outline of this operating system can also represented by FIG. 7, wherein the x- and y-axes in units of time. These axes then serve to present an organized data structure within time. Again, the z-axis represents information transport conducted either by a flow of atoms, electrons, photons or molecules.

In another embodiment, the operating system of ditom can be employed to integrate molecular information by classes of matter, as indicated by defining x in Eq. 1 in units of matter, cell or organism. The outline of this operating system can also be represented by FIG. 7, wherein the x- and y-axes relate to some physical property associated with a given classification of matter. These axes then serve to present an organized data structure within time. Again, the z-axis represents information transport conducted either by a flow of atoms, electrons, photons, or molecules.

Figure 8:
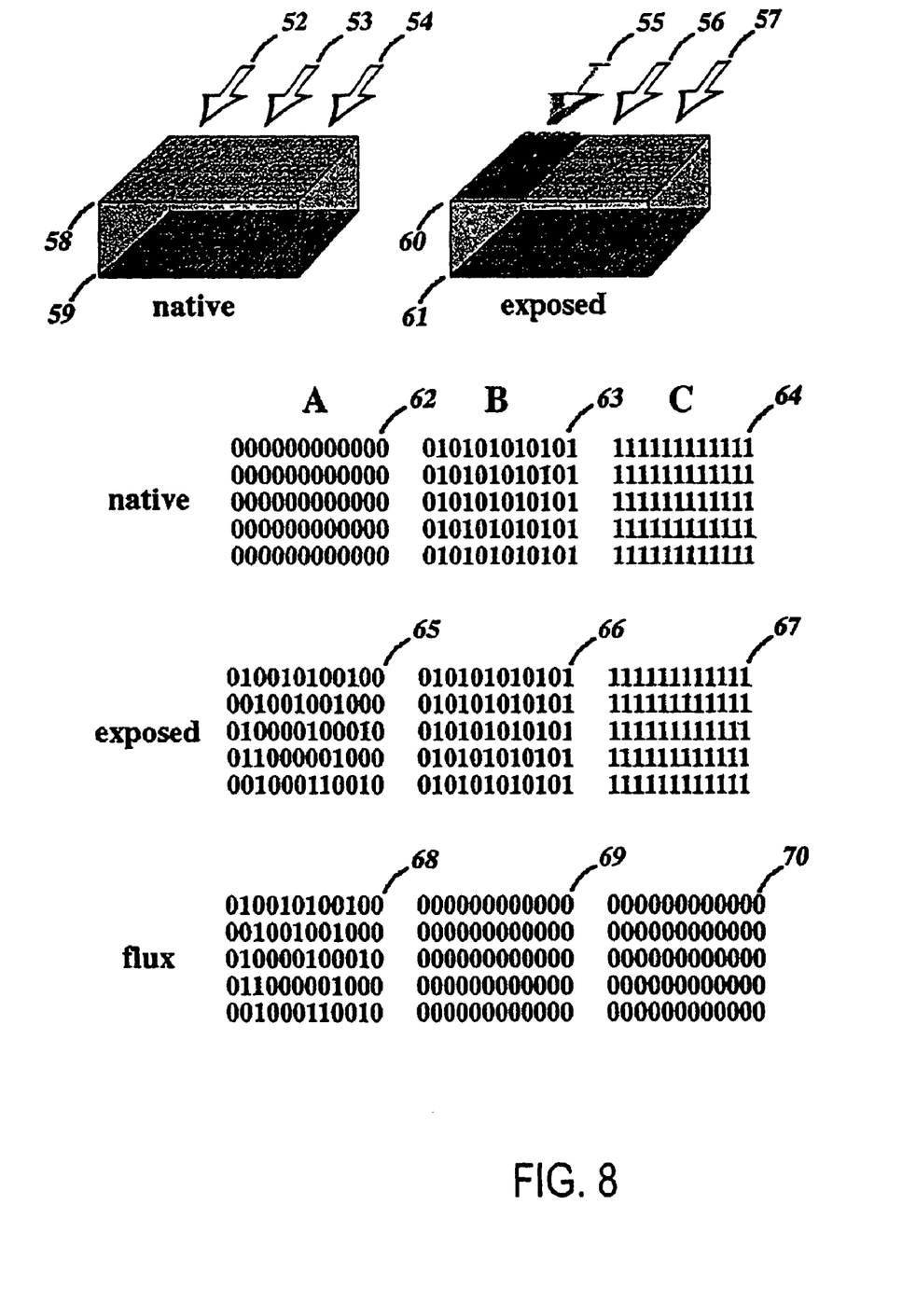
In FIG. 8, the physical structuring of ditom is described.
Figure 9:
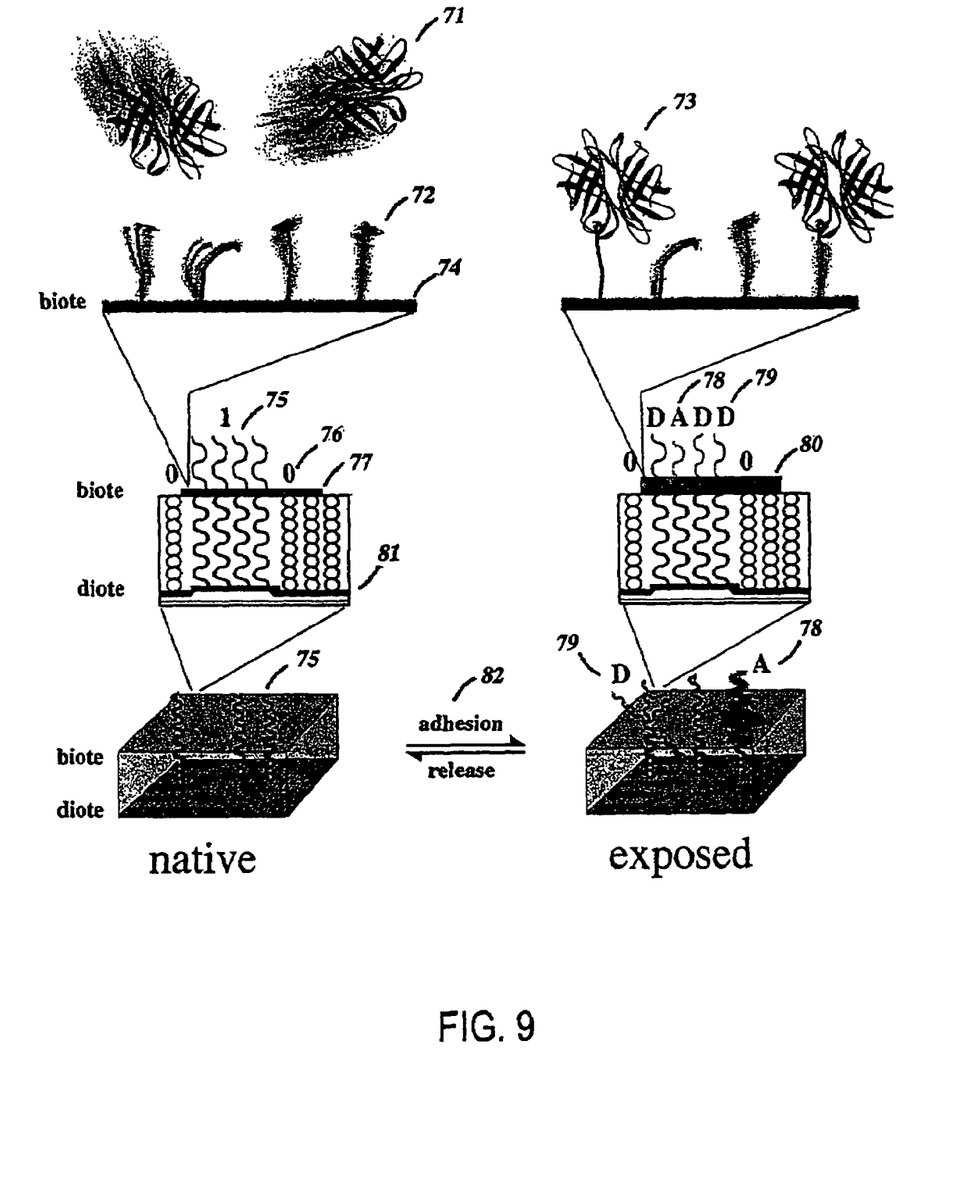
In FIG. 9, an example underling how the affinity between streptavidin and biotin alter the communication between a creator and its processor is shown. This system is displayed in three magnifications, decreasing in magnitude as passing from top to bottom.

A physical structure of the operating system outlined in FIG. 8 can be expressed in terms of FIG. 9. For simplicity purposes, this demonstration is illustrated with but not limited to recognizing streptavidin by its binding to biotin. In the native state, streptavidin (71) remains unbound and floats freely in molecular space. In this state, surface-expressed biotinylated-receptors (72) gyrates harmonically through an organized program of molecular dynamics. While each molecule exists at a given time in a unique state, the collection of these states over a given period of time and geometric space remains uniform. Therefore, the density expressed over the biotic surface (74) in the remains constant. When exposed the manipulator (85), streptavidin binds to surface-expressed biotinylated-receptors (73). This manipulator can be represented by a range of physical functions and can arise from manipulating geographical positioning, force, temperature, time, and/or field. This binding causes changes in the surface density and altars transmission of the underling digital code. A illustrated in the middle row, digital information is transmitted from the underling diotic layer (81) through the biotic layer (77) either encoded as an active signal (75) or passive signal (76). The difference between (75) and (76) represent a digital system. As a molecule is added the substrate changes from (77) to (80). This manipulation alters the format of the active signal (75) either by absorbing (78) or distorting (79) it. Correspondingly, this manipulation can also alter the passive signal (76) by enhancing or distorting it (not shown). In this system, the diotic (83) layer can either be the creator or a part of the substrate. The biotic layer (77) must serve as a part of the substrate. Information from sent from the diotic layer (81) passes through the biotic layer (73) to a processor, as indicated in all three perspectives provided in FIG. 9.

b. Structure

Division into smaller subsections readily distinguishes the structure of this operating system. As defined, each biote corresponds to a single molecular reaction or sensor. The biotic layer is devised such that its entire structure is correlates with a given diote. This layer can be printed or displayed or expressed or released into or onto the diote.

Figure 10:
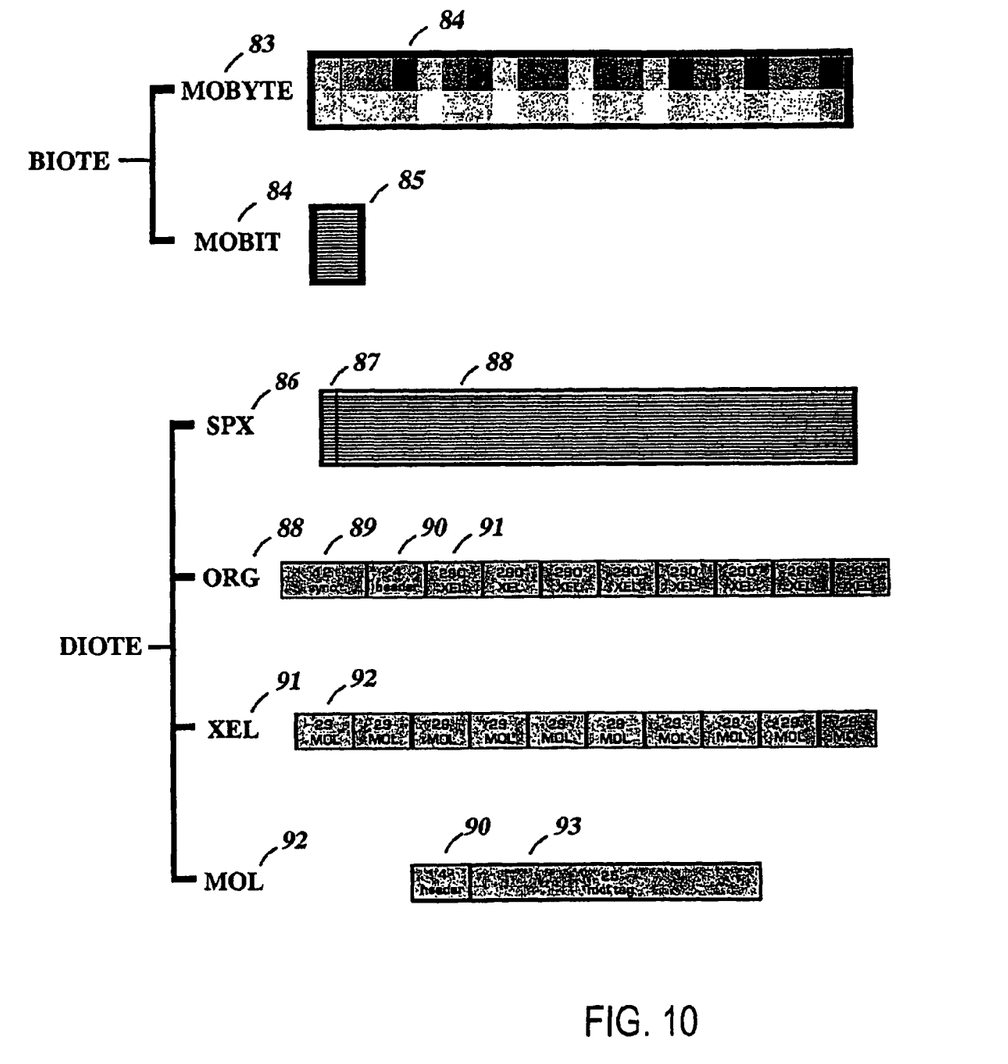
Figure 11:
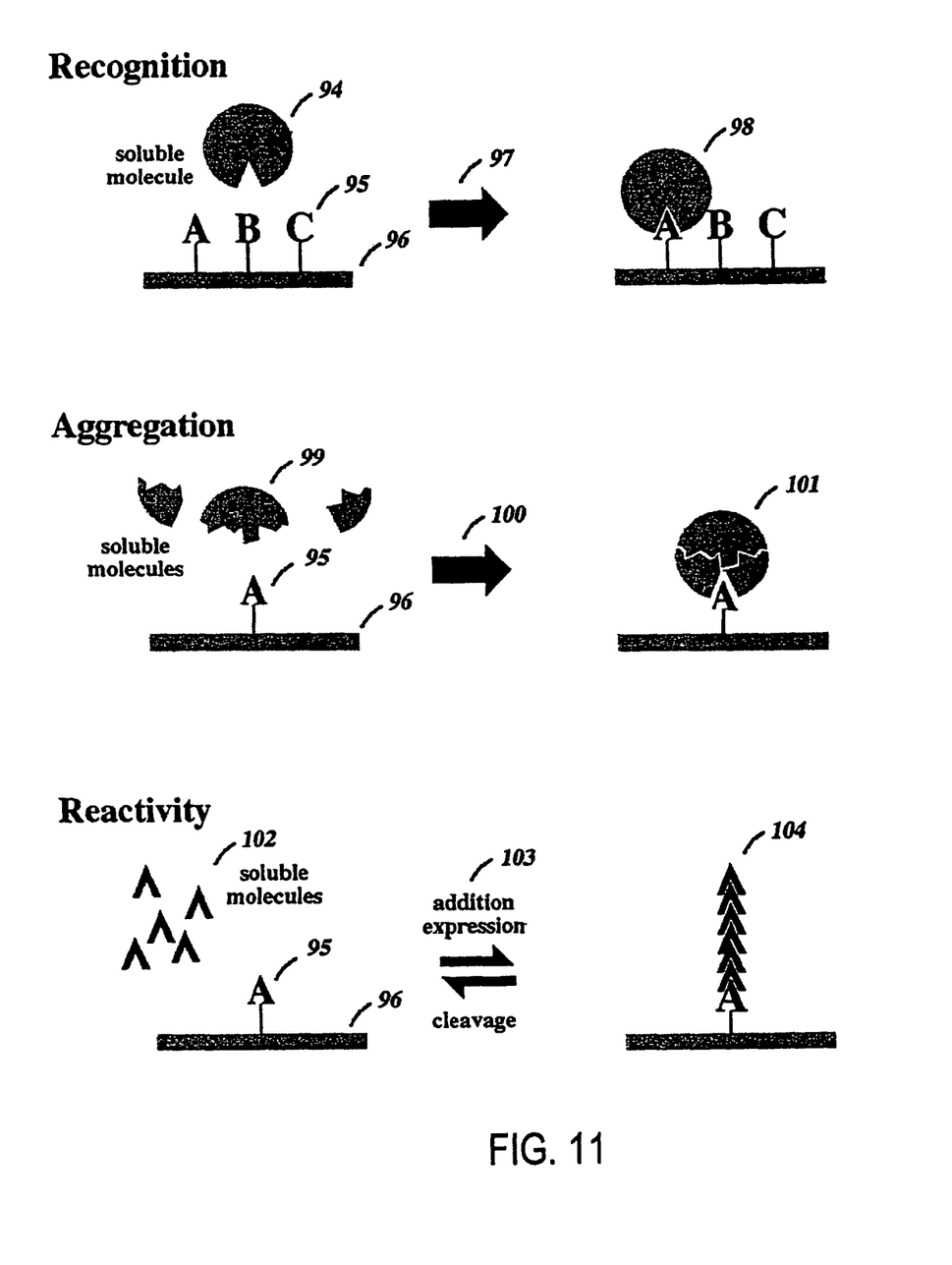

For the cursory model to function in FIGS. 8-9, the diotes must expand from small data sets to megabytes of digital data. Each operating system described herein and developed therefrom has a given size and nature of its biote-diote pair. As defined, each diote must directly correlates with a biote. For organization purposes, the diote is broken down in to a series of information stages (FIG. 10). The first of which is called an SPX (86). The SPX (89) begins with a within a 16-bit signature (88). This signature serves to identify the system or method used to communicate the ditom. For instance, a signature of 0000011000000011 would describe a given optical system, while another microelectronic system would have a signature of 0001001001001001. Each SPX is broken down into ORGs (87). An ORG (87) begins with a 12-sync coded (89) used to align the ORG in the SPX and 4-bit header (90) followed 8 XELs (91). Each XEL is composed of 10 repeating units called MOLs (92). The MOL(90) is the basic unit of the diotic layer. It is comprised of the 4-bit header (90) and a mol tag ranging. This mol tag serves to specifically identify a given molecular species.

For example, streptavidin could be encoded by a 25 bit mol tag of 0010000100001000010000100 (93), and accompanied by a header 0101 (90), sync code of 011011011011 (89) and signature of 0000011000000011 (88).

This example would then have a MOL (92) of (- added for visibility):
-0101-0010000100001000010000000;
a XEL (91) of:
-0101-0010000100001000010000100-0101-
0010000100001000010000100-0101-

0010000100001000010000100-0101-
0010000100001000010000100-0101-
0010000100001000010000100-0101-
0010000100001000010000100-01010-
0010000100001000010000100-0101-
0010000100001000010000100-0101-
0010000100001000010000100-0101-
0010000100001000010000100
and ORG (88) of:
011011011011-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100-0101-
0010000100001000010000100

The SPX for this example would be prepared by assembling a collection or string or array of the preceding ORGs. This SPX or collections thereof serves as the diote. This diote is positioned in a dimension of time or space such that it directly correlates with the biote or biote.

c. Operation

Series of both exposed and native diotes are then read over a series of readings, by using the appropriate physical device to monitor the transfer of a prescribed digitally encoded function. The data collected from the native set is then subtracted from the exposed set. The absolute value of this data set serves as flux $\zeta$. This flux therefore defines each bit of 0 as a bit remain the same, and 1 if the bit was converted from 1 to 0 or 0 to 1. Bits that were altered but whose identity due to the randomness of error remain invisible after one reading. These are called devoid bits. By using multiple readings, these bits devoid bits are corrected for. As illustrated in the bottom of FIG. 8, bits that differed hence 1's, appears only in the region that underlies receptor A. This new data set expresses the flux, and therein represents a means to digitally-encode a molecular event.

d. Applications

Ditom can be used to monitor any molecular interaction or processes that involve the addition or subtraction of molecular mass. This include manipulations arising from binding (either through aggregation, complexation and/or recognition), growth (through expression), or release (through reactivity) of two or group of molecules. A brief introduction to each category follows.

Recognition

The recognition between two molecules can be used to determine the identity of a certain molecular species. As illustrated in the top of FIG. 10, the structure of the given soluble molecule (94) allows it to bind receptor A but not to other receptors B or C. The binding of (94) to A on a given substrate (96), induced by manipulator (97), creates a new complex (98). The structure and expression of this new complex disturbs the translation of a given digital stream creating a flux. This scheme can be used applied to a wide range of natural and synthetic materials, and is particularly applicable to identify antibodies, carbohydrates, genes, growth factors, proteins and other biologically relevant small molecules.

Association

Molecular association either in solution or on a cell surface serves to signal a wide range of intra- and extra-cellular process. The nature of these responses relies not only on the identity of each species but also on the ability of each molecule to appropriately associate. Ditom provides a means to rapidly screen molecular aggregation by appropriately tuning the surface bound microprobe. As indicated in the middle of FIG. 10, the binding of a group of unrelated or unrelated molecules (99) to receptor A (95) on a given substrate (96) increases the molecular structure (101) causing the flux in the transmission of ditomic data.

Reactivity

In addition to molecular recognition and aggregation, ditome can also be applied monitor the concentration and reactivity of a molecule, thereby extending utility of this technology to screen for catalysis and biochemical viability. As illustrated on the bottom of FIG. 10, flux increases as more manipulator alters the substrate (96). As illustrated here, this system can be used to monitor cleavage or addition reactions. In one state, molecules (102) remains soluble, leaving the substrate (96) and receptor (95) transparent. In a second state, the (102) can be covalently-bound to the surface as illustrated by (104). The amount of each states can be manipulated (103) by a given reaction or chemical species. This manipulation (103) can also be defined by comparing the effect that the given manipulation has on flux associated with the relative population of both states.

The information collected from the aforementioned chemical phenomena can be used for a wide range of applications including but not limited to: expedite medical diagnostics, communicating medical information, develop personal based security systems and extend entertainment systems.

e. Demonstration

To illustrate, the operating system of ditom is defined to model that is compatible with the optical train of a compact disc player. This demonstration serves to illustrate the function of ditom however in no means restrict the operating system of ditom for application to compact disc technologies or other optical storage devices.

This demonstration began by preparing a new disc format. This format and operation of this disc is unique and remains distinct from other disc systems described for molecular diagnostics including U.S. Pat. No. 6,030,581. The disk described here operates using the rotary system and optical train of a CD player or CD-ROM drive or DVD player, more over this system requires no spheres, capillary ducts, valves, batteries, dialyzers, columns, filters, or electrical fields as previously described in U.S. Pat. No. 6,030,581. This disc advantageously allows the user to directly read molecules without complicated attaching tags or incorporation of spheres.

Figure 12:
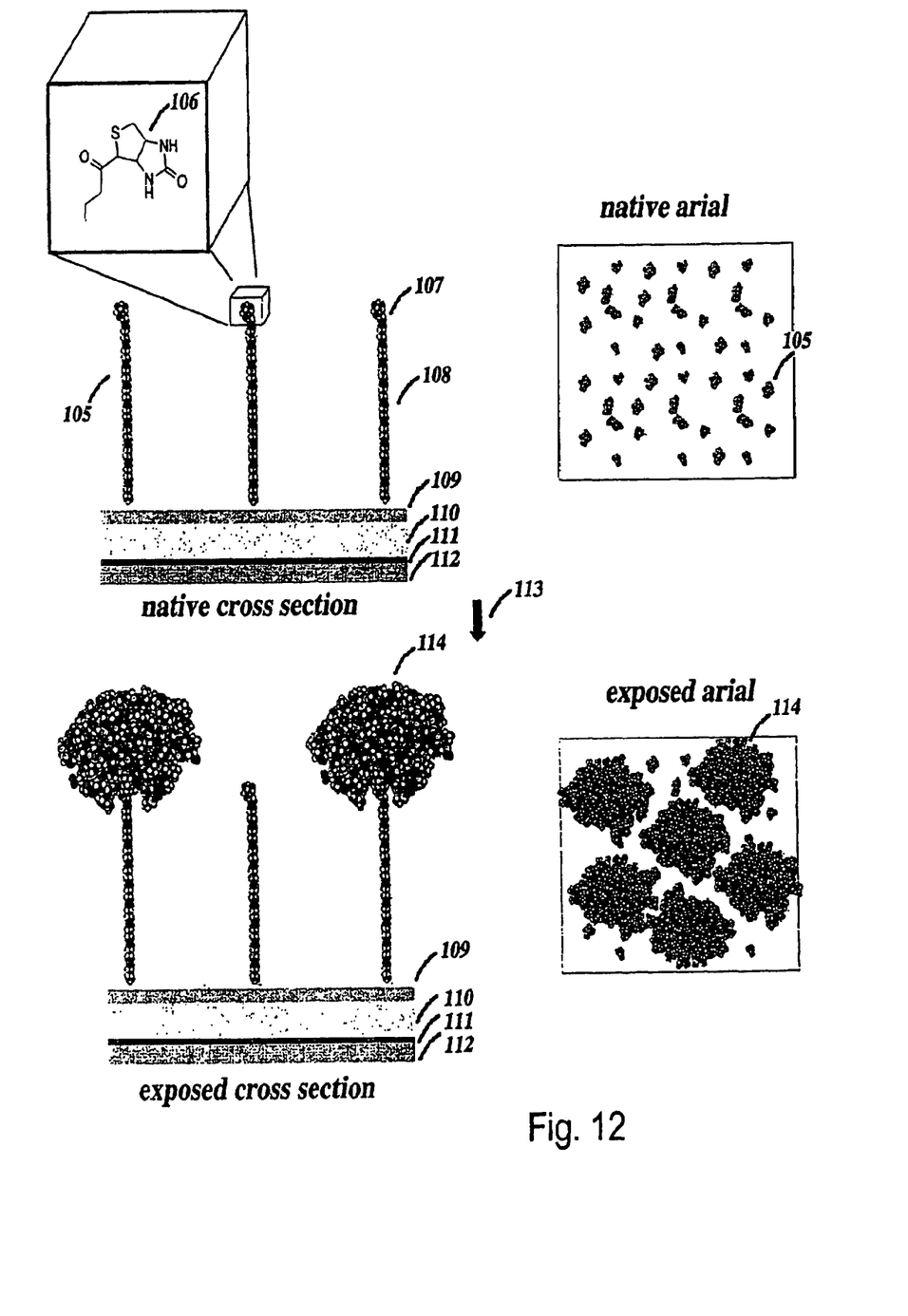
In FIG. 12, an application of ditom to read molecular recognition as indicated here by the interaction between biotinylated receptor (105) and streptavidin (110) is shown. This example is demonstrated by application to but not limited to compact disc technology.

The disc is composed of a series of four layers (FIG. 12). The bottom three layers (110-112) mimic that used by CD-ROM XA. The second layer serves as the diotic layer (111). The diotic (111), acrylic layer (112) and polycarbonate (110) layers were created using a masking technologies comparable to that described in U.S. Pat. Nos. REF. For purposes of simplicity, the example demonstrated herein was executed using an diotic structure whose bit density was comparable to that CD-ROM XA and contained repeated SPX such that its structure fit the spatial area required necessary for the biote. As illustrated in FIG. 10, the SPX (86) contained a 40 signatures of 0000011000000011 (87) followed by 40 horizontally-stacked ORGs with a sync (89) of 011011011011, a header (90) guided by CD-ROM XA tracking and a MOL of 001000010000100001000100, as illustrated prior in section IIb.

A biotic layer (109) was printed on top of the polycarbonate layer (110). This layer consists of a mono-functionalized receptor (105) containing a spacer (106) and a molecule specific binding site (107). This spacer can be any repetitive chemical element that bears low chemical reactivity. For the purpose of this demonstration, polyethylene glycol 500 was used, wherein one side of the glycol was attached to the surface of the disc. This spacer could be placed either over the entire disc or within specific sections using conventional laser printing with a resolution reproducible within a pixel dimension of greater than 10 $\mu M \times 10$ $\mu M$. The biotic layer was then created on this surface using the diotic data. This process serves as part of the native creator (5). This disc was placed within a two-laser player whose function bears similarity to that described for CD-write and CD-RW systems. The disc was then covered with a 400 $\mu M$ thick adhesive sheet whose bottom side is coated a solution of biotinylated-probe (105) in a resin. The coating is placed on the disc such that the resin layer is in direct contact with the upper or biotic surface of the disc. This system was devised such that laser beam 1 reads the disc. The diotic data, read from the disc and stored within a computers memory, was then replayed by software and used to instruct the second laser beam to heats the surface of the disc where the given diote was expressed. Heating initiates a chemical reaction that binds the biotinylated-probe (107) with structure (106) to the top of the spacer (107), providing surface bound receptor (105). In order to ensure coverage of the diote, the software was programmed to thermally print the receptors in an area that was 10% enhanced in all dimensions. As illustrated here, the code described diotic layer creates the biotic layer.

Figure 13:
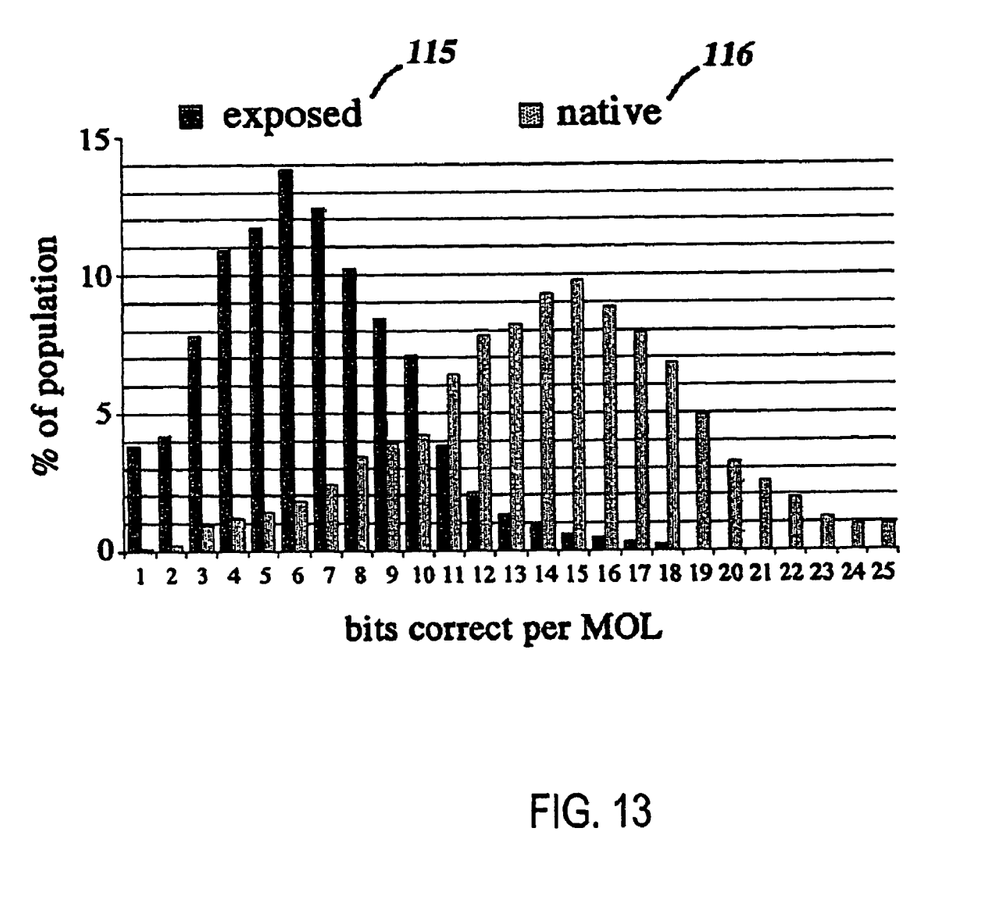
In FIG. 13, the outcome of applying ditom to screen the recognition of streptavidin by a biotin containing biote-diote pair is shown.

Using this system, receptor (105) was arrayed to within 2,500 $\mu M2$. Within these dimensions, thermal printing of this biotic layer covers the entire expanse of the underling diote (FIG. 12). The biotic layer or top of this disc (see arial view in FIG. 12) was then exposed to a series of biological probes one of which contained streptavidin. After exposure, the disc was soaked in bath of PBS for 20 min to ensure maximal removal molecular matter that lacked receptor specificity were removed to biotin-encoded surface. The disc was then washed with sterile deionized water and dried by wiping with a cotton or dust free cloth. The diotic layer of these discs was then read by placing the disc in a ROM CD-RW or DVD player of personal computer and instructing software to read the disc. As indicated in FIG. 12, this reading process must pass through biotic surface, which now contains (114). The addition of streptavidin to the surface (114) now alters the molecular dynamics of the surface (best seen in arial views on the right of FIG. 12), generating a layer whose molecular density and dynamics is inconsistent. As shown, regions of this surface now contain significant buildup of protein mass. At programmable doping, this mass lacks uniformity and certain regions of the surface remain more transparent. This now imperfect structure either absorbs or deflects the reflected light generated when hitting land, digitally expressed by 1 (FIG. 9). This alteration creates error in reading both the active (land) and passive (pits) regions. This error is then expressed within the diotic data read by the player. While the physical structure of the diotic layer has not changed, its structure and identity has. A disc created with a biote with a length of 7 mm and width of 4 mm was stretched along a concentric track of a disc such that it covered a 9.4 megabyte diote comprised one hundred 94,080 bit long SPX built packed in two adjacent 50 column stacks. The native state of this disc was then read by placing it in a 12× CD-ROM drive of a Macintosh PowerBook 1400 cs/113 and reading the specific tracking covering the biote 10 times. Each MOL was then extracted and compared to its known structure. The amount of erroneous bits per MOL was determined and this data is presented in FIG. 13. This disc was exposed by treating for 5 min in dish containing 100 ml of 1 pM solution streptavidin in PBS, removed, soaked for 20 min in sterile PBS, washed with a deionized water, and then wiped with a cotton or lint free cloth. This process serves as the manipulator. The disc was then placed back in the same CD-ROM drive and read over the same tracking 10 times. The 9.4-Mb diote was then compared over the 10 readings, using the aforementioned method the flux seen in each MOL was then determined. As seen in FIG. 13, the exposed state (115) that contains considerably more flux than that seen when examining the native state (116). Most importantly, exposure of the disc to solutions of other non- biotin binding proteins (i.e. 100 ml of 50 nM of BSA in PBS) did not generate (115) rather provided a spectrum that was within 0.05% of the native structure (116).

In this application, the ditomic layer served with the disc reader and computer as the creator (5 or 9). The ditomic data was used to create the biotic layer, which in turn served as the native (6) and exposed (10) substrates. The manipulator (8) consisted of exposing the biotic layer with a biological sample, washing and then drying it. This action changed the substrate (6) to (10), as seen by (105) to (110). This change altered the bit structure transferred from the creator or diotic layer and received by the appropriate processor (7 vs. 11). Data illustrated in FIG. 13 depicts flux within the MOLs of the diotic layer as they were received by the manipulated processor (11). FIG. 13 serves to digitally characterize a spectrum for a given molecule. Most importantly, the creator and processor use the bit network.

ADVANCES

The subject matter according to the invention describes a new operating system for diagnosing molecular information called for example ditom. In part, this embodiment illustrated the function and operating system of ditom for optically storage of CD technology. The operating system of ditom however can be extended to a variety of systems including operations wherein, diotic bits are defined within other spatial elements, time or even by a given molecular feature. These systems can include alteration of wide range of digitally encoded physical properties, including the transfer of optical, electronic, molecular, or magnetic streams or fields, wherein the data structured by the creating body and that examined by the processing body maintain the identical or a mathematically-related structure.

The major advance extended lies in its simplicity in reduced encoding. Most importantly, this simplicity allows both the creation and examination processes to rapidly interact with modern instruments of digital communications. The use of a single encoding system also allows the operating system to compare and connect its creator and processing units to better define the nature and operation of the substrate. This connection can be used to build an artificially intelligent system wherein the creator and processor remains one unit and learns by manipulation to organize and process itself.

The information gathered by this operating system serve to define a new level of molecular communication. Systems built hereon define a new level of technology, and extend a variety of tools for medicinal examination and/or scientific research, and further define new instruments for education and entertainment.

The invention claimed is:

1. A method for identifying molecular species, said method comprising the steps of
   creating at least one stream of binary data carried by electrical, molecular or light signals,
   transferring the at least one stream of binary data carried by electrical, molecular or light signals through a substrate;
   allowing interaction of molecules or groups of molecules with the substrate;
   receiving the streams of binary data carried by electrical, molecular or light signals transferred through the substrate; and
   decoding the identity of an examined molecule or group of molecules interacting with the substrate according to the alteration of the stream of binary data carried by electrical, molecular or light signals obtained during the transmission of the at least one stream of binary data carried by electrical, molecular or light signals through the substrate.

2. The method according to claim 1, wherein the stream of binary data carried by electrical, molecular or light signals is altered during its transfer through the substrate according to a mathematical or programmable function.

3. The method according to claim 1, wherein the step of creating includes generating a digitally encoded photon flux.

4. The method according to claim 3, wherein the photon flux includes a beam or group of beams consisting of polarized, non-polar, monochromatic or broad banned light.

5. The method according to claim 1, wherein the step of creating includes generating an array of molecules that can operate in a binary manner.

6. The method according to claim 1, wherein the step of creating includes generating digital electronic signals by gating electron flow over a two or a three dimensional space.

7. The method according to claim 1, wherein the step of manipulating includes adding or subtracting molecules or groups of molecules.

8. The method according to claim 7, wherein the manipulating includes use of heat, light, gravity, centripetal action, and/or pressure.

9. The method according to claim 7, wherein the manipulating is performed on either a two-dimensional surface or a three-dimensional element.

10. The method of claim 1, wherein decoding the identity of an examined molecule or group of molecules interacting with the substrate includes detecting an alteration in the stream of binary data resulting from a change on the substrate correlated with a surface bound receptor.

11. A device for identifying molecular species, said device comprising
    creating means that release at least one stream of binary data carried by electrical, molecular or light signals,
    transferring means that transfer the at least one stream of binary data carried by binary electrical, molecular or light signals through a substrate;
    manipulating means for manipulating the molecular structure of the substrate by adding or subtracting molecules or groups of molecules to be examined to or from the substrate;
    receiving means for receiving the at least one stream of binary data carried by electrical, molecular or light signals transferred through the substrate; and
    decoding means for decoding the identity of an examined molecule or group of molecules interacting with the substrate according to the alternation of the at least one stream of binary data carried by electrical, molecular or light signals obtainable during the transmission of the at least one stream of binary data carried by electrical, molecular or light signals through the substrate.

12. The device according to claim 11, wherein the creating means include an optical system that generates a digitally encoded photon flux.

13. The device according to claim 12, wherein the photon flux includes a beam or group of beams consisting of polarized, non-polar, monochromatic or broad banned light.

14. The device according to claim 12, wherein the creating means include a microelectronic system that generates an array of molecules that can operate in a binary manner.

15. The device according to claim 12, wherein the creating means include a microelectronic component that generates digital electronic signals by gating electron flow over a three dimensional space.

16. The device according to claim 15, wherein the microelectronic component includes an entity that either stores, processes, transfers or creates electron flow.

17. The device according to claim 11, wherein the manipulating means includes an element that adds or subtracts a molecular entity.

18. The device according to claim 11, wherein the manipulating includes use of heat, light, gravity, centripetal action, and/or pressure.

19. The device according to claim 11, wherein the manipulating is performed on either a two-dimensional surface or a three-dimensional element.

20. The device of claim 11, wherein the decoding means for decoding the identity of an examined molecule or group of molecules interacting with the substrate includes means for detecting an alteration in the at least one stream of binary resulting from a change on the substrate correlated with a surface bound receptor.

* * * * *